| (12) | United States Patent | (10) Patent No.: | US 7,396,535 B2 |
|---|---|---|---|
| | Ackerman | (45) Date of Patent: | Jul. 8, 2008 |

(54) THERAPY FOR OBSESSIVE COMPULSIVE HEAD BANGING

(76) Inventor: Alan H. Ackerman, 1722 26th Ave. Ct., Greeley, CO (US) 80634

( * ) Notice: Subject to any disclaimer, the term of this patent is extended or adjusted under 35 U.S.C. 154(b) by 194 days.

(21) Appl. No.: 10/423,778

(22) Filed: Apr. 25, 2003

(65) Prior Publication Data

US 2004/0213813 A1   Oct. 28, 2004

(51) Int. Cl.
```
A61K 39/00        (2006.01)
A61K 39/02        (2006.01)
A61K 39/08        (2006.01)
```
(52) U.S. Cl. .............. 424/247.1; 424/184.1; 424/234.1; 424/236.1

(58) Field of Classification Search .............. 424/184.1, 424/236.1, 239.1, 247.1
See application file for complete search history.

(56) References Cited

U.S. PATENT DOCUMENTS

| 5,437,291 | A | 8/1995 | Pasricha et al. |
|---|---|---|---|
| 5,670,484 | A | 9/1997 | Binder |
| 5,714,468 | A | 2/1998 | Binder |
| 5,766,605 | A | 6/1998 | Sanders et al. |
| 5,989,545 | A | 11/1999 | Foster et al. |
| 6,063,768 | A | 5/2000 | First |
| 6,113,915 | A | 9/2000 | Aoki et al. |
| 6,139,845 | A | 10/2000 | Donovan |
| 6,143,306 | A | 11/2000 | Donovan |
| 6,265,379 | B1 | 7/2001 | Donovan |
| 6,299,893 | B1 | 10/2001 | Schwartz et al. |
| 6,306,403 | B1 | 10/2001 | Donovan |
| 6,306,423 | B1 | 10/2001 | Donovan et al. |
| 6,312,708 | B1 | 11/2001 | Donovan |
| 6,328,977 | B1 | 12/2001 | Donovan |
| 6,358,513 | B1 | 3/2002 | Voet et al. |
| 6,365,164 | B1 | 4/2002 | Schmidt |
| 6,395,277 | B1 | 5/2002 | Graham |
| 6,423,319 | B1 | 7/2002 | Brooks et al. |
| 6,458,365 | B1 | 10/2002 | Aoki et al. |
| 6,464,986 | B1 | 10/2002 | Aoki et al. |
| 6,620,415 | B2 * | 9/2003 | Donovan .................. 424/239.1 |
| 6,688,311 | B2 * | 2/2004 | Hanin ......................... 128/898 |
| 6,689,816 | B2 | 2/2004 | Fogel ......................... 514/702 |
| 6,955,813 | B2 | 10/2005 | Brooks et al. ............ 424/239.1 |
| 2001/0053370 | A1 | 12/2001 | Donovan .................. 424/239.1 |
| 2003/0234727 | A1 | 12/2003 | Perlman .................... 340/573.1 |
| 2004/0157926 | A1 | 8/2004 | Heresco-Levy et al. ..... 514/561 |
| 2006/0286127 | A1 | 12/2006 | Van Schaack et al. ..... 424/239.1 |

OTHER PUBLICATIONS

Jankovic, Neurology 1993, Apr. 43 (4 Supp 2).*
Jankovic, Movement Disorders, vol. 9, No. 3, 1994).*
Schantz et al, Microbiological Reviews, Mar. 1992, p. 80-92.*
Granana et al, Seminars in Pediatric Neurology, Sep. 6, 1999, Vo. 6. No. 3, pp. 221-224.*
Hashizume et al, (Psychiatry and Clinical Neurosciecnes (2002), 56, 255-256).*
Granana et al (Seminars in Pediatric Neurology, Sep. 6, 1999, vol. 6. No. 3, pp. 221-224).*
Hashizume et al (Psychiarty and Clinical Neurosciecnes (2002), 56, 255-256).*
Hsiung et al (Movement Disorders: Official Journal of Movement Disorder Society, Nov. 1001, 17(6), 1288-93) (Abstract only).*
Micheli et al (Clinical Neuropharmacology Sep.-Oct. 2002, Vo. 25, No. 5, pp. 2606-263) (Abstract only).*
Denislic et al (Annals of the New York Academy of Sciences, Mar. 9, 1994, 710, p. 76-87).*
Stedmans's Medical Dictionary, 24, Edition, Williams & Wilkins.*
Leung et al (J Singapore Paediatr. Soc., 1990; 32(1-2):14-17).*
Micheli et al (Clinical Neuropharmacology, Sep.-Oct. 2002, vol. 25, No. 5, p. 260-262). (Abstract only).*
U.S. Appl. No. 10/423,380, filed Mar. 25, 2003, Alan H. Ackerman.
U.S. Appl. No. 10/423,384, filed Mar. 25, 2003, Alan H. Ackerman.
U.S. Appl. No. 10/424,050, filed Mar. 25, 2003, Alan H. Ackerman.
U.S. Appl. No. 10/424,009, filed Mar. 25, 2003, Alan H. Ackerman.
Aoki, K.R. et al., Botulinum toxin type A and other botulinum toxin serotypes: a comparative review of biochemical and pharmacological actions; *European Journal Neurology*; 2001; 8 (Suppl 5):pp. 21-29.
Aoki, K.R.; Physiology and Pharmacology of Therapeutic Botulinum Neurotoxins; In: Kreyden OP, ed. *Hyperhidrosis and Botulinum Toxin in Dermatology*; Current Problems in Dermatology: Basel, Karger; 2002; 30: pp. 107-116.
Bigalke, Hans et al., Botulinum A Neurotoxin Inhibits Non-Cholinergic Synaptic Transmission in Mouse Spinal Cord Neurons in Culture; *Brain Res*; 1985; 360: pp. 381-424.

(Continued)

*Primary Examiner*—Shanon A. Foley
*Assistant Examiner*—Vanessa L. Ford
(74) *Attorney, Agent, or Firm*—Claude L. Nassif; Stephen Donovan; Martin A. Voet

(57) ABSTRACT

Methods for treating a head banging disorder by local administration of a *Clostridial* toxin. The local administration can be by intramuscular, transdermal, intradermal or subdermal administration of a low dose of *botulinum* toxin.

4 Claims, No Drawings

OTHER PUBLICATIONS

Bigalke, H. et al., Tetanus Toxin and Botulinum A Toxin Inhibit Release and Uptake of Various Transmitters, as Studied with Particulate Preparations from Rat Brain and Spinal Cord; *Naunyn Schmiedebergs Arch Pharmacol*; 1981; 316; pp. 244-251.

Binz, Thomas et al., The Complete Sequence of Botulinum Neurotoxin Type A and Comparison with Other Clostridial Neurotoxins; *J Biochem*; (Tokyo) Jun. 5, 1990; 265(16); pp. 9153-9158.

Brem, Henry et al., Placebo-controlled trial of safety and efficacy of intraoperative controlled delivery by biodegradable polymers of chemotherapy for recurrent gliomas; *The Lancet*;vol. 345; Apr. 22, 1995; pp. 1008-1012.

Brin, Mitchell F. et al., Botulinum Toxin Type A: Pharmacology; In: Mayer Nathaniel H, ed. *Spasticity: Etiology, Evaluation, Management and the Role of Botulinum Toxin*; 2002; pp. 110-124.

Chappell, Phillip et al., Future Therapies of Tourette Syndrome; *Neurol Clin*; 1997; vol. 15, No. 2, May; pp. 429-450.

Cui, M. et al., Mechanisms of the Antinociceptive Effect of Subcutanous Botox® : Inhibition of Peripheral and Central Nociceptive Processing; *Naunyn Schmiedebergs Arch Pharmacol*; 2002; 365 (Suppl 2) R17; Abstract.

Dabrowski, E. et al., Botulinum Toxin as a Novel Treatment for Self Mutilation in Lesch-Nyhan Syndrome; *Ann Neurol*; 2002; 52(3): S157; Abstract.

Duggan, Michael J. et al., A survey of botulinum neurotoxin substrate expression in cells; *Mov Disord*; 1995; May; 10(3) p. 376.

Fauci et al., *Harrison's Principles of Internal Medicine*; 14th ed.

Ferrari, David M. et al., The protein disulphide-isomerase family: unravelling a string of folds; *Biochem J*; 1999 (339) pp. 1-10.

Fung, Lawrence K. et al., Pharmacokinetics of Interstitial Delivery of Carmustine, 4-Hydroperoxycyclophosphamide, and Paclitaxel from a Biodegradable Polymer implant in the Monkey Brain; *Cancer Research*; 58, Feb. 15, 1998; pp. 672-684.

Guyton, Arthur C. et al., *Textbook of Medical Physiology 10th ed*; W.B. Saunders Company, pp. 686-688.

Habermann, E., I-Labeled Neurotoxin from Clostridium Botulinum A: Preparation, Binding to Synaptosomes and Ascent to the Spinal Cord; *Naunyn Schmiedeberg's Arch. Pharmacol*; 1974; (281); pp. 47-56.

Habermann, E., Inhibition by tetanus and botulinum A toxin of the release of {3H}noradrenaline and {3H}GABA from rat brain homogenate; *Experientia*; Mar. 15, 1988; 44(3) pp. 224-226.

Habermann, E. et al., Tetanus Toxin and Botulinum A and C Neurotoxins Inhibit Noradrenaline Release from Cultured Mouse Brain; *J Neurochem*; vol. 51, No. 2 1988; pp. 522-527.

Jankovic, Joseph; Botulinum Toxin in the Treatment of Dystonic Tics; *Movment Disorders*; vol. 9, No. 3, 1994; pp. 347-349.

Jankovic, Joseph; Botulinum Toxin in the Treatment of Tics Associated with Tourette's Syndrome; *Neurology*; Apr. 1993; 43(4 Suppl 2); A310; Abstract.

Jankovic, Joseph et al., *Therapy with Botulinum Toxin*; Marcel Dekker, Inc.; pp. 71-85; also p. 5 and 150.

Krauss, Joachim K. et al., Severe Motor Tics Causing Cervical Myelopathy in Tourette's Syndrome; *Movement Disorders*; vol. 11, No. 5, 1996; pp. 563-565.

Kudelko, K.M. et al., Successful treatment of recalcitrant restless legs syndrome with botulinum toxin A; *Movment Disorders*; 2002; 17 (Suppl 5); S242 ABS p779.

Marjama-Lyons, Jill et al., Tremore-Predominant Parkinson's Disease; *Drugs & Aging*; Apr. 16, 2000; (4) pp. 273-278.

Naumann, Markus et al., Botulinum Toxin type A in the treatment of focal, axillary and palmar hyperhidrosis and other hyperhidrotic conditions; *European Journal of Neurology*; 1999, vol. 6 (suppl 4) pp. S111-S115.

Pearce, Bruce et al., Pharmacologic Characterization of Botulinum toxin for Basic Science and Medicine; *Toxicon*; 1997; 35 (9); pp. 1373-1412.

Ragona, Rosario M. et al., Management of Parotid Sialocele With Botulinum Toxin; *Laryngoscope*; 109; Aug. 1999 (8); pp. 1344-1346.

Sanchez-Prieto, Jose et al., Botulinum toxin A blocks glutamate exocytosis from guinea-pig cerebral cortical synaptosomes; *Eur J Biochem*; Jun. 1987; 165 (3); pp. 675-681.

Schantz, Edward J. et al., Properties and Use of Boulinum Toxin and Other Microbial Neurotoxins in Medicine; *Microbiol Review*; Mar. 1992; 56 (1); pp. 80-99.

Singh, Bal Ram; Critical Aspects of Bacterial Protein Toxins; *Natural Toxins II*; Edited by B. R. Singh et al., Plenum Press, New Yrok, 1996; Chapter 4, pp. 63-84.

Sloop, Richard R. et al., Reconstituted botulinum toxin type A does not lose potency in humans if it refrozen or refrigerated for 2 weeks before use; *Neurology*; Jan. 1997; 48 (1); pp. 249-253.

Wiegand, H. et al., I-Labelled Botulinum A Neurotoxin: Pharmacokinetics in Cats after intramuscular Injection; *Naunyn Schmiedebergs Arch Pharmacol*; 1976; 292; pp. 161-165.

Zigmond, et al., *Fundamental Neuroscience*; 1999 by Academic Press, San Diego, CA; pp. 963-964.

Ahn, et al., Plast. Reconstr. Surg., 105, 2002, pp. 778-784 (abstract).

Arezzo, et al., Pain Med. 2, 202, 239, Sep. 2001 (abstract).

Arnold et al., J. Clin. Psychiatr., 59, 1998, pp. 509-514 (Abstract).

Awad, et al., J. Chil. Neurol., 14, 1999, pp. 316-319.

Berardelli et al., Italian J. Neurol. Sci., 18, 1997, pp. 261-269.

Berkson, Gershon, et al., Body-Rocking and Other Habits of College Students and Persons With Mental Retardation, American Journal on Mental Retardation, 1999, vol. 104, No. 2, pp. 107-116.

Callaway, et al., Sem. Cutan. Med. Surg., Jun. 20, 2001, pp. 127-136.

Canafoglia, Laura, et al., Rhythmic Cortical Myoclonus.In A Case Of HIV-Related Encephalopathy, Mov. Disord., 2003, 18(12).

Czaplinksi, A., et al., Tic Syndrome, (article in Polish), Neurol Neurochir Pol., Nov.-Dec. 2000, 36(6), pp. 1251-1253.

Dabrowski, et al., Dev. Med. Child Neurol., 47, 2005, pp. 636-639.

Diagnostic and Statistical Manual of Mental Disorders, 4th Edition, Published by the American Psychiatric Association, Washington, D.C., pp. 108-116.

Frankel, et al., Neurology, 36, 1986, pp. 378-382.

George, et al., Ann. Otol. Rhinol. Laryngol., 101, 1992, pp. 888-892 (abstract).

Ghika, J., et al., Bilateral contemporaneous posteroventral pallidotomy for the tratment of Parkinson's disease: neuropsychological and neurological side effects. Report of four cases and review of the literature, J. Neurosurg, Aug. 1999, 91(2), pp. 313-321.

Giladi, N., et al., J. Neurol. Sci., 152, 1997, pp. 132-135 (abstract).

Greenberg, et al., Neruology, 54, 2000, pp. 142-147.

Jankovic, J., In: Therapy with Botulium Toxin (Ed) Jankovic J., Chapter 39, 1994, pp. 503-509.

Jimenez-Jimenez, F.J., et al., Pharmacological options for the treatment of Tourette's disorder, Drugs, 2001, 61(15), pp. 2207-2220.

Keythen et al., Psychosomatics 42, 2001, pp. 397-403.

Kossoff, et al., Tourette Syndrome: Clinical Characteristics and Current Management Strategies, Paediatric Drugs, 3(5), 2001, pp. 355-363.

Krack, P., et al., Modification of a Facial Tick with Botulinum Toxin, Mov Disord, May 1995, 10(3), p. 401.

Kwak, C., et al., Premonitory sensor phenomenon in Tourette's syndrome, Mov. Disord., Dec. 2003, 18(12), pp. 1530-1533.

Kwak, Carolyn, et al., Tics in Tourette Syndrome and Botulinum Toxin, Journal of Child Neurology, 15(9), Sep. 2000.

Kwak, et al., Botulinum Toxin in the Treatment of Tics, Arch. Neurol., 57, 2000, pp. 1190-1193.

Lang, A., Neurology, 41, 1991, pp. 223-228.

Lang, A.E., Update on the Treatment of Tics, Adv. Neurol., 2001, 85, pp. 355-362.

Lang, et al., Adv. Neurol. 58, 1992, pp. 25-32.

Lavenstein, B.L., Treatment Approaches for Children with Tourette's Syndrome, Curr Neurol Neurosci Rep., Mar. 2003 3(2), pp. 143-148.

Leckman, et al., Am. J. Psychiatry, 150, 1993, pp. 98-102.

Leckman, et al., Am. J. Psychiatry, 151, 1994, pp. 675-680.

Lee, et al., J. Clin Psychol. 32, 1976, pp. 843-844 (abstract).

Marras, et al., Neurology, 56, Mar. 2001, pp. 605-610.

Matarasso, S.L., Dermatol. Surg., 29, 2001, pp. 7-13 (abstract).

Moyer, Elizabeth, et al., Botulinum Toxin Type B: Experimental and Clinical Experience, In: Jankovic, J., (Ed.) Neurological Disease and Therapy. Therapy with Botulinum Toxin, 1994, 25, pp. 71-85.

Murry et al., Arch. Otolaryngol. Head Neck Surg., 120, 1994, pp. 310-316.

Naver, et al., Eur. J. Neurol., Jan. 7, 2000, pp. 55-62.

Pauls, et al., Arch. Gen. Psychiatry, 43, 1986, pp. 1180-1182.

Pigott et al., J. Clin. Psychiatr., 1994, 55 Suppl., pp. 15-27.

Poungvarin, et al., J. Med. Assoc. Thailand, 78, 1995, pp. 281-288.

Pranzatelli, Michael R., Antidyskinetic Drug Therapy for Pediatric Movement Disorders, Journal of Child Neurology, vol. 11, No. 5, Sep. 1996, pp. 355-369.

Prytz, S., et al., Treatment of Vocal Tics in Tourette's Syndrome with Injection of Botulinum Toxin in the Vocalis Muscle: A Case Report, European Journal of Neurology, 7 (Suppl. 3), 2000, pg. 143.

Report of the Therapeutics and Technology Assessment Subcommittee of the American Academy of Neurology, Neurology 40, 1990, pp. 1332-1336.

Robertson, J. Child Psychol. Psychiatr., 35, 1994, pp. 597-611.

Rodriguez-Nunez, Antonio, Syncope and Seizures: It is time for Evidence! Journal of Child Neurology, 15(9), Sep. 2000.

Salloway, Stephen, et al., Botulinum Toxin for Refractory Vocal Tics, Mov Disord 1996 11(6), pp. 746-748.

Schapiro, Pediatric Nursing, 28, May-Jun. 2002, pp. 243-253.

Scott, B.L., et al., Botulinum toxin injection into vocal cord in the treatment of malignant coprolalia associated with Tourette's syndrome, Mov. Disord., Jul. 1996, 11(4), pp. 431-433.

Singer, H.S., et al., New Treatments for Tourette's Syndrome, Inpharma 21 Spr 2001 No. 1284.

Stein et al., J. Clin. Psychiatr., 58, Apr. 1997, pp. 177-178.

Sugahara, H., et al., Psychogenic torticollis,. (article in Japanese), Ryoikibetsu Shokogun Shirizu, 2003, 38, pp. 582-586.

Trimble, Michael R., et al., Vocal Tics in Gilles de la Tourette Syndrome Treated with Botulinum Toxin Injections, Mov Disord May 1998 13(3), pp. 617-619.

Wang, C., & Curry, L., (Eds.), Symptomatology: Motor and Phonic Tic Manifestations, Tourette Syndrome: A Continuing Education Course for Registered Nurses, Tourette Syndrome Association, Southern California Chapter, Oct. 19, 2004, pp. 1-3.

Weinlander et al., J. Psychol. 34, 1978, pp. 31-32 (abstract).

Weinlander et al., J. Psychol. 92, 1976, pp. 77-78 (abstract).

Wohlfarth, et al., Naunyn Schmiedebarg's Arch. Pharmacol., 355, 1997, pp. 335-340.

* cited by examiner

THERAPY FOR OBSESSIVE COMPULSIVE HEAD BANGING

BACKGROUND

The present invention relates to methods for treating certain obsessive compulsive disorders. In particular, the present invention includes methods for treating various repetitive and/or injurious motor activity symptoms of certain obsessive compulsive disorders by peripheral administration of a *Clostridial* toxin.

Obsessions are persistent ideas, thoughts, impulses or mental images that cause distress and anxiety. Obsessions can involve themes of aggression, contamination, sex or somatic concerns. Compulsions are repetitive, stereotyped motor acts an individual feels required to perform to reduce anxiety or distress. The compulsion usually can be resisted only temporarily, with resistance followed by an increasing sense of unease and tension. The mounting tension is released only by performing the irrational motor act or ritual. Compulsions very in complexity from simple actions such as touching, lip licking, tapping and rubbing to complex behaviors such as repetitive hand washing, hair pulling and body rocking. Additionally, compulsive behaviors can include hoarding, repeating, checking (i.e. repeated checking that a door is locked), counting (i.e. compulsive counting of footsteps) and arranging behaviors, as well as various self-injurious behaviors, such as self-biting (i.e. finger biting), head banging, eye poking, skin picking, skin cutting, skin burning, eye enucleation and castration. Unfortunates with such disturbing self-injurious compulsions must frequently be restrained or fitted with suitable restraints (such as a mouth guard) to prevent further injury to themselves. These compulsions can be severely disabling and can accompany psychosis, intoxication, Tourette's syndrome and mental retardation.

Thus, obsessive compulsive disorders can combine both obsessive thoughts and compulsive behaviors, and can be defined as a chronic condition characterized by recurrent intrusive thoughts and ritualistic behaviors that consume much of the afflicted person's attention and activity, thereby impairing everyday functioning. The behaviors of an obsessive and/or compulsive disorder typically begin in late childhood or early adulthood and the patient experiences marked tension and distress upon resisting the obsessions and compulsions. Epidemiologic data indicates a lifetime prevalence of 2 to 3 percent worldwide and obsessive compulsive disorders are more common in males and in first born children. See e.g. page 2490 of Fauci, A. S. et a., editors, *Harrison's Principles of Internal Medicine*, McGraw Hill, fourteenth edition (1998).

Functional neuroimaging (i.e. positron emission tomography) studies, brain lesion analysis, and the results of neurosurgical intervention to treat obsessive compulsive disorders indicate that dysfunction within particular basal ganglia and ventral prefrontal cortical structures provides a proposed pathophysiology for obsessive compulsive disorders. See e.g. pages 963-964 of Zigmond, M. J. et al, editors, *Fundamental Neuroscience*, Academic Press (1999).

Clearly, obsessive compulsive disorders can cause great embarrassment, distress and anguish to both the cognizant patient so afflicted as well as to his or her caregiver.

Tourette's Syndrome

Tourette's syndrome is usually characterized by multiple motor tics and one or more vocal tics. The tics can appear simultaneously or at different periods during the illness. The tics can occur many times a day and recurrently throughout a period of more than one year. During this period, there is almost never a tic-free period of more than a few consecutive months. Those afflicted with Tourette's syndrome suffer disturbances which can comprise complex tics and cause marked distress or significant impairment in social, occupational, and other important areas of functioning. The onset of the disorder is typically before the age of eighteen. The complex tics of Tourette's syndrome are not due to the direct physiological effects of a substance (e.g., stimulants) or a general medical condition (e.g., Huntington's disease or postviral encephalitis) and are thought to be a part of the Tourette's disease process. The anatomical location, number, frequency, complexity, and severity of the tics often change over time. The tics typically involve the head and, frequently, other parts of the body, such as the torso and upper and lower limbs. The vocal tics include various words or sounds such as clicks, grunts, yelps, barks, sniffs, snorts, and coughs. Coprolalia (a complex vocal tic involving the uttering of obscenities), is present in a few individuals (less than 10%) with this disorder. Complex motor tics involving touching, squatting, deep knee bends, retracing steps, and twirling when walking may be present. In approximately one-half the individuals with this disorder. The first symptoms to appear are often bouts of a single tic, most frequently eye blinking, less frequently tics involving another part of the face or the body. Initial symptoms can also include tongue protrusion, squatting, sniffing, hopping, skipping, throat clearing, stuttering, uttering sounds or words, and coprolalia.

Whereas the repetitive motor activities symptomatic of Tourette's syndrome can be characterized as true tics (that is, as habitual, repeated contraction of certain muscles, as in throat clearing, sniffing, lip pursing or excessive blinking) they are an isolated and distinct subset of behaviors distinct from obsessive compulsive disorders, as defined by the Diagnostic and Statistical Manual of the American Psychiatric Association (the "DSM-IVR", fourth revised edition). There are a number of obsessive and/or compulsive disorders which involve more complex non tic repetitive motor activity, frequently injurious, as can occur in dermatillomania, trichotillomania, hand washing, head banging, eye poking, body rocking, finger biting, counting, and checking disorders.

Dermatillomania (Compulsive Skin Picking)

The primary characteristic of compulsive skin picking is the repetitive picking at one's own skin to the extent of causing damage. Usually, but not always, the face is the primary location for skin picking. However compulsive skin picking, also known as dermatillomania or neurotic excoriation, can involve any part of the body. Individuals with compulsive skin picking may pick at normal skin variations such as freckles and moles, at actual pre-existing scabs, sores or acne blemishes, or at imagined skin defects that nobody else can observe. The compulsive skin picking patient may use his or her fingernails, as well as their teeth, tweezers, pins or other mechanical devices. As a result, dermatillomania can cause bleeding, bruises, infections, and/or permanent disfigurement of the skin.

Sometimes skin-picking is preceded by a high level of tension and a strong itch or urge to pick. Likewise, carrying out the skin-picking can be followed by a feeling of relief or pleasure. A compulsive skin picking episode can be a conscious response to anxiety or depression, but is frequently done as an unconscious habit. Individuals with compulsive skin picking often attempt to camouflage the damage caused to their skin by using make-up or wearing clothes to cover the subsequent marks and scars. In extreme cases, individuals with compulsive skin picking avoid social situations in an effort to prevent others from seeing the scars, scabs, and bruises that result from skin picking.

The primary treatment modality for compulsive skin picking depends on the level of awareness the individual has regarding the problem. If the compulsive skin picking is generally an unconscious habit, the primary treatment is a form of cognitive-behavioral therapy called habit reversal training (HRT). HRT is based on the principle that skin-picking is a conditioned response to specific situations and events, and that the individual with compulsive skin picking is frequently unaware of these triggers. HRT challenges the problem in a two-fold process. First, the individual with compulsive skin picking learns how to become more consciously aware of situations and events that trigger skin-picking episodes. Second, the individual learns to utilize alternative behaviors in response to these situations and events. Unfortunately HRT does not have a high success rate. If the patient is unaware of or not fully cognizant of his compulsive skin picking, pharmacologic therapy is recommended. Significant side effects have occurred from the current drug therapy.

Trichotillomania (Compulsive Hair Pulling)

Trichotillomania (TTM) is a compulsive disorder where the patient pulls out his or her hair from the scalp, eyelashes, eyebrows, or other parts of the body, resulting in noticeable bald patches. Thus symptoms of trichotillomania includes recurrent pulling out of one's hair resulting in noticeable hair loss, and this is usually preceded by an increasing sense of tension immediately before pulling out the hair or when resisting the behavior, followed by pleasure, gratification, or relief while the hair is being pulled out. This disorder can cause significant distress and impairment in social, occupational, or other important areas of functioning. It is estimated that trichotillomania affects one to two percent of the population, or four to eleven million Americans. TTM seems to strike most frequently in the pre-or early adolescent years. The typical first-time hair puller is 12 years old, although TTM has affected people as young as one and as old as seventy. About ninety percent of those with TTM are women.

Although the symptoms range greatly in severity, location on the body, and response to treatment, most people with TTM pull enough hair over a long enough period of time that they have bald spots on their heads (or missing eyelashes, eyebrows, pubic, or underarm hair), which they go to great lengths to cover with hairstyles, scarves or clothing, or makeup. The persistence of the compulsion can vary considerably, at times; the urge may be so strong that it makes thinking of anything else nearly impossible.

Treatments for TTM include behavioral therapy and drugs. In behavioral therapy, patients learn a structured method of keeping track of the symptoms and associated behaviors, increasing awareness of pulling, substituting incompatible behaviors and several other techniques aimed at reversing the "habit" of pulling. Although medications clearly help some people temporarily, symptoms are likely to return when the medication is stopped unless behavioral therapy is incorporated into treatment. Medications may help to reduce the depression and any obsessive-compulsive symptoms the person may be experiencing. Commonly used medications include fluoxetine (Prozac), fluvoxamine (Luvox), sertraline (Zoloft), paroxetine (Paxil), clomipramine (Anafranil), valproate (Depakote), and lithium carbonate (Lithobid, Eskalith). Unfortunately, behavioral therapies have limited success, and the drugs therapies can have significant side effects and require regular, chronic repeat dosings.

Thus, there are many drawbacks and deficiencies with current obsessive compulsive disorder therapies. Treatment regimes available include chronic administration of drugs which inhibit serotonin reuptake (such drugs are called SSRIs or serotonin reuptake inhibitors) and behavior modification therapies. Clomipramine, fluoxetine and fluvoxamine are approved for the treatment of obsessive compulsive disorders. Notably, clomipramine is a tricyclic antidepressant which is poorly tolerated due to significant anticholinergic and sedative side effects. Additionally, fluoxetine and fluvoxamine (SSRIs) also have a side affect profile, which can include cardiac arrhythmias, although they tend to be more benign that clomipramine. Furthermore, only about 50 to 60 percent of patients with an obsessive compulsive disorder show an acceptable degree of improvement when either or both pharmacotherapies, and behavior modification strategies have been tried.

Botulinum Toxin

The genus *Clostridium* has more than one hundred and twenty seven species, grouped according to their morphology and functions. The anaerobic, gram positive bacterium *Clostridium botulinum* produces a potent polypeptide neurotoxin, *botulinum* toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The *botulinum* toxin can apparently pass unattenuated through the lining of the gut and attack peripheral motor neurons. Symptoms of *botulinum* toxin intoxication can progress from difficulty walking, swallowing, and speaking to paralysis of the respiratory muscles and death.

*Botulinum* toxin type A is the most lethal natural biological agent known to man. About 50 picograms of a commercially available *botulinum* toxin type A (purified neurotoxin complex[1] is a LD50 in mice (i.e. 1 unit). One unit of BOTOX® (a *botulinum* toxin type A purified neurotoxin complex, which is also referred to as a *botulinum* toxin type A complex) contains about 50 picograms (about 56 attomoles) of *botulinum* toxin type A complex. Interestingly, on a molar basis, *botulinum* toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63-84 (chapter 4) of Natural Toxins II, edited by BR. Singh et al., Plenum Press, New York (1976) (where the stated LD50 of *botulinum* toxin type A of 0.3 ng equals 1 U is corrected for the fact that about 0.05 ng of BOTOX® (a *botulinum* toxin type A complex) equals 1 unit). One unit (U) of *botulinum* toxin is defined as the LD50 upon intraperitoneal injection into female Swiss Webster mice weighing 18 to 20 grams each.

[1] Available from Allergan, Inc., of Irvine, Calif. under the tradename BOTOX® (a *botulinum* toxin type A complex) in 100 unit vials)

Seven generally immunologically distinct *botulinum* neurotoxins have been characterized, these being respectively *botulinum* neurotoxin serotypes A, B, $C_1$, D, E, F and G each of which is distinguished by neutralization with type-specific antibodies. The different serotypes of *botulinum* toxin vary in the animal species that they affect and in the severity and duration of the paralysis they evoke. For example, it has been determined that *botulinum* toxin type A is 500 times more potent, as measured by the rate of paralysis produced in the rat, than is *botulinum* toxin type B. Additionally, *botulinum* toxin type B has been determined to be non-toxic in primates at a dose of 480 U/kg which is about 12 times the primate $LD_{50}$ for *botulinum* toxin type A. Moyer E et al., *Botulinum Toxin Type B: Experimental and Clinical Experience*, being chapter 6, pages 71-85 of "Therapy With *Botulinum* Toxin", edited by Jankovic, J. et al. (1994), Marcel Dekker, Inc. *Botulinum* toxin apparently binds with high affinity to cholinergic motor neurons, is translocated into the neuron and blocks the release of acetylcholine. Additional uptake can take place through low affinity receptors, as well as by phagocytosis and pinocytosis.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of *botulinum* toxin and for *tetanus* toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of *botulinum* toxin activity appears to involve reduction of the disulfide bond joining the heavy chain, H chain, and the light chain, L chain. The entire toxic activity of *botulinum* and *tetanus* toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. *Tetanus* neurotoxin, *botulinum* toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. *Botulinum* toxin serotype A and E cleave SNAP-25. *Botulinum* toxin serotype $C_1$ was originally thought to cleave syntaxin, but was found to cleave syntaxin and SNAP-25. Each of the *botulinum* toxins specifically cleaves a different bond, except *botulinum* toxin type B (and *tetanus* toxin) which cleave the same bond. Each of these cleavages block the process of vesicle-membrane docking, thereby preventing exocytosis of vesicle content.

*Botulinum* toxins have been used in clinical settings for the treatment of neuromuscular disorders characterized by hyperactive skeletal muscles (i.e. motor disorders). In 1989 a *botulinum* toxin type A complex has been approved by the U.S. Food and Drug Administration for the treatment of blepharospasm, strabismus and hemifacial spasm. Subsequently, a *botulinum* toxin type A was also approved by the FDA for the treatment of cervical dystonia and for the treatment of glabellar lines, and a *botulinum* toxin type B was approved for the treatment of cervical dystonia. Non-type A *botulinum* toxin serotypes apparently have a lower potency and/or a shorter duration of activity as compared to *botulinum* toxin type A. Clinical effects of peripheral intramuscular *botulinum* toxin type A are usually seen within one week of injection. The typical duration of symptomatic relief from a single intramuscular injection of *botulinum* toxin type A averages about three months, although significantly longer periods of therapeutic activity have been reported.

Although all the *botulinum* toxins serotypes apparently inhibit release of the neurotransmitter acetylcholine at the neuromuscular junction, they do so by affecting different neurosecretory proteins and/or cleaving these proteins at different sites. For example, *botulinum* types A and E both cleave the 25 kiloDalton (kD) synaptosomal associated protein (SNAP-25), but they target different amino acid sequences within this protein. *Botulinum* toxin types B, D, F and G act on vesicle-associated protein (VAMP, also called synaptobrevin), with each serotype cleaving the protein at a different site. Finally, *botulinum* toxin type $C_1$ has been shown to cleave both syntaxin and SNAP-25. These differences in mechanism of action may affect the relative potency and/or duration of action of the various *botulinum* toxin serotypes. Apparently, a substrate for a *botulinum* toxin can be found in a variety of different cell types. See e.g. *Biochem J* 1;339 (pt 1):159-65:1999, and *Mov Disord*, 10(3):376:1995 (pancreatic islet B cells contains at least SNAP-25 and synaptobrevin).

The molecular weight of the *botulinum* toxin protein molecule, for all seven of the known *botulinum* toxin serotypes, is about 150 kD. Interestingly, the *botulinum* toxins are released by *Clostridial bacterium* as complexes comprising the 150 kD *botulinum* toxin protein molecule along with associated non-toxin proteins. Thus, the *botulinum* toxin type A complex can be produced by *Clostridial bacterium* as 900 kD, 500 kD and 300 kD forms. *Botulinum* toxin types B and $C_1$ is apparently produced as only a 700 kD or 500 kD complex. *Botulinum* toxin type D is produced as both 300 kD and 500 kD complexes. Finally, *botulinum* toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the *botulinum* toxin molecule comprise the relevant neurotoxin complex) may act to provide stability against denaturation to the *botulinum* toxin molecule and protection against digestive acids when toxin is ingested. Additionally, it is possible that the larger (greater than about 150 kD molecular weight) *botulinum* toxin complexes may result in a slower rate of diffusion of the *botulinum* toxin away from a site of intramuscular injection of a *botulinum* toxin complex.

In vitro studies have indicated that *botulinum* toxin inhibits potassium cation induced release of both acetylcholine and norepinephrine from primary cell cultures of brainstem tissue. Additionally, it has been reported that *botulinum* toxin inhibits the evoked release of both glycine and glutamate in primary cultures of spinal cord neurons and that in brain synaptosome preparations *botulinum* toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain*, J Neurochem 51(2);522-527:1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165;675-681:1897. Thus, when adequate concentrations are used, stimulus-evoked release of most neurotransmitters is blocked by *botulinum* toxin. See e.g. Pearce, L. B., *Pharmacologic Characterization of Botulinum Toxin For Basic Science and Medicine*, Toxicon 35(9);1373-1412 at 1393; Bigalke H., et al., *Botulinum A Neurotoxin Inhibits Non-Cholinergic Synaptic Transmission in Mouse Spinal Cord Neurons in Culture*, Brain Research 360;318-324:1985; Habermann E., *Inhibition by Tetanus and Botulinum A Toxin of the release of [³H]Noradrenaline and [³H]GABA From Rat Brain Homogenate*, Experientia 44;224-226:1988, Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316;244-251:1981, and; Jankovic J. et al., *Therapy With Botulinum Toxin*, Marcel Dekker, Inc., (1994), page 5.

*Botulinum* toxin type A can be obtained by establishing and growing cultures of *Clostridium botulinum* in a fermenter and then harvesting and purifying the fermented mixture in accordance with known procedures. All the *botulinum* toxin serotypes are initially synthesized as inactive single chain proteins which must be cleaved or nicked by proteases to become neuroactive. The bacterial strains that make *botulinum* toxin serotypes A and G possess endogenous proteases and serotypes A and G can therefore be recovered from bacterial cultures in predominantly their active form. In contrast, *botulinum* toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the *botulinum* toxin type B serotype only cleave a portion of the toxin produced. The exact proportion of nicked to unnicked molecules depends on the length of incubation and the temperature of the culture. Therefore, a certain percentage of any preparation of, for example, the *botulinum* toxin type B toxin is likely to be inactive, possibly accounting for the known significantly lower potency of *botulinum* toxin type B as compared to *botulinum* toxin type A. The presence of inactive *botulinum* toxin molecules in a clinical preparation will contribute to the overall protein load of the preparation, which has been linked to increased antigenicity, without contributing to its clinical efficacy. Additionally, it is known that *botulinum* toxin type B has, upon intramuscular injection, a shorter duration of activity and is also less potent than *botulinum* toxin type A at the same dose level.

High quality crystalline *botulinum* toxin type A can be produced from the Hall A strain of *Clostridium botulinum* with characteristics of $\geq 3 \times 10^7$ U/mg, an $A_{260}/A_{278}$ of less than 0.60 and a distinct pattern of banding on gel electrophoresis. The known Shantz process can be used to obtain crystalline *botulinum* toxin type A, as set forth in Shantz, E. J., et al, *Properties and use of Botulinum toxin and Other Microbial Neurotoxins in Medicine*, Microbiol Rev. 56;80-99:1992. Generally, the *botulinum* toxin type A complex can be isolated and purified from an anaerobic fermentation by cultivating *Clostridium botulinum* type A in a suitable medium. The known process can also be used, upon separation out of the non-toxin proteins, to obtain pure *botulinum* toxins, such as for example: purified *botulinum* toxin type A with an approximately 150 kD molecular weight with a specific potency of $1-2 \times 10^8$ $LD_{50}$ U/mg or greater; purified *botulinum* toxin type B with an approximately 156 kD molecular weight with a specific potency of $1-2 \times 10^8$ $LD_{50}$ U/mg or greater, and; purified *botulinum* toxin type F with an approximately 155 kD molecular weight with a specific potency of $1-2 \times 10^7$ $LD_{50}$ U/mg or greater.

*Botulinum* toxins and/or *botulinum* toxin complexes can be obtained from List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo. Pure *botulinum* toxin can also be used to prepare a pharmaceutical composition.

As with enzymes generally, the biological activities of the *botulinum* toxins (which are intracellular peptidases) is dependant, at least in part, upon their three dimensional conformation. Thus, *botulinum* toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can stabilized with a stabilizing agent such as albumin and gelatin.

A commercially available *botulinum* toxin containing pharmaceutical composition is sold under the trademark BOTOX® (a *botulinum* toxin type A complex (available from Allergan, Inc., of Irvine, Calif.). BOTOX® (a *botulinum* toxin type A complex) consists of a purified *botulinum* toxin type A complex, albumin and sodium chloride packaged in sterile, vacuumdried form. The *botulinum* toxin type A is made from a culture of the Hall strain of Clostridium *botulinum* grown in a medium containing N-Z amine and yeast extract. The *botulinum* toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® (a *botulinum* toxin type A complex) can be reconstituted with sterile, non-preserved saline prior to intramuscular injection. Each vial of BOTOX® (a *botulinum* toxin type A complex) contains about 100 units (U) of Clostridium *botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX® (a *botulinum* toxin type A complex), sterile normal saline without a preservative; (0.9% Sodium Chloride Injection) is used by drawing up the proper amount of diluent in the appropriate size syringe. Since BOTOX® (a *botulinum* toxin type A complex) may be dispersed or denatured by bubbling or similar violent agitation, the diluent is gently injected into the vial. For sterility reasons BOTOX® (a *botulinum* toxin tyne A comylex) is preferably administered within four hours after the vial is removed from the freezer and reconstituted. During these four hours, reconstituted BOTOX® (a *botulinum* toxin type A complex) can be stored in a refrigerator at about 2° C. to about 8° C. Reconstituted, refrigerated BOTOX® (a *botulinum* toxin type A complex) has been reported to retain its potency for at least about two weeks. *Neurology*, 48:249-53:1997.

It has been reported that botulinum toxin type A has been used in clinical settings as follows:
(1) about 75-125 units of BOTOX® (a *botulinum* toxin type A complex) per intramuscular injection (multiple muscles) to treat cervical dystonia;
(2) 5-10 units of BOTOX® (a *botulinum* toxin type A complex) per intramuscular injection to treat glabellar lines (brow furrows) (5 units injected intramuscularly into the procerus muscle and 10 units injected intramuscularly into each corrugator supercilii muscle);

(3) about 30-80 units of BOTOX® (a *botulinum* toxin type A complex) to treat constipation by intrasphincter injection of the puborectalis muscle;

(4) about 1-5 units per muscle of intramuscularly injected BOTOX® (a botutinum toxin type A complex) to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX® (a *botulinum* toxin type A complex), the amount injected varying based upon both the size of the muscle to be injected and the extent of muscle paralysis desired (i.e. amount of diopter correction desired).

(6) to treat upper limb spasticity following stroke by intramuscular injections of BOTOX® (a *botulinum* toxin type A complex) into five different upper limb flexor muscles, as follows:
(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® (a *botulinum* toxin type A complex) by intramuscular injection at each treatment session.

(7) to treat migraine,pericranial injected (injected symmetrically into glabellar, frontalis and temporalis muscles) injection of 25 U of BOTOX® (a *botulinuni* toxin tyne A complex) has showed significant benefit as a prophylactic treatment of migraine compared to vehicle as measured by decreased measures of migraine frequency, maximal severity, associated vomiting and acute medication use over the three month period following the 25 U injection.

Additionally, intramuscular *botulinum* toxin has been used in the treatment of tremor in patients with Parkinson's disease, although it has been reported that results have not been impressive. Marjama-Jyons, J., et al., *Tremor-Predominant Parkinson's Disease*, Drugs & Aging 16(4);273-278:2000.

It is known that *botulinum* toxin type A can have an efficacy for up to 12 months (*European J. Neurology*6 (Supp 4): S111-S1150:1999), and in some circumstances for as long as 27 months, when used to treat glands, such as in the treatment of hyperhydrosis. See e.g. Bushara K., *Botulinum toxin and rhinorrhea*, Otolaryngol Head Neck Surg 1996;114(3):507, and The Laryngoscope 109:1344-1346:1999. However, the usual duration of an intramuscular injection of BOTOX® (a *botulinum* toxin type A complex) is typically about 3 to 4 months.

The success of *botulinum* toxin type A to treat a variety of clinical conditions has led to interest in other *botulinum* toxin serotypes. Two commercially available *botulinum* type A preparations for use in humans are BOTOX® (a *botulinum* toxin type A complex) available from Allergan, Inc., of Irvine, Calif., and DYSPORT® (a *botulinum* toxin tyne A complex) available from Beaufour Ipsen, Porton Down, England. A *Botulinum* toxin type B preparation (MYOBLOC®) is available from Elan Pharmaceuticals of San Francisco, Calif.

In addition to having pharmacologic actions at the peripheral location, *botulinum* toxins may also have inhibitory effects in the central nervous system. Work by Weigand et al, *Naunv-Schmiedeberg's Arch. Pharmacol.* 1976; 292, 161-165, and Habermann, *Nauny-Schmiedeberg's Arch. Pharmacol.* 1974; 281, 47-56 showed that *botulinum* toxin is able to ascend to the spinal area by retrograde transport. As such, a *botulinum* toxin injected at a peripheral location, for example intramuscularly, may be retrograde transported to the spinal cord.

U.S. Pat. No. 5,989,545 discloses that a modified *clostridial* neurotoxin or fragment thereof, preferably a *botulinum* toxin, chemically conjugated or recombinantly fused to a particular targeting moiety can be used to treat pain by administration of the agent to the spinal cord.

A *botulinum* toxin has also been proposed for the treatment of rhinorrhea, hyperhydrosis and other disorders mediated by the autonomic nervous system (U.S. Pat. No. 5,766,605), tension headache, (U.S. Pat. No. 6,458,365), migraine headache (U.S. Pat. No. 5,714,468), post-operative pain and visceral pain (U.S. Pat. No. 6,464,986), pain treatment by intraspinal toxin administration (U.S. Pat. No. 6,113,915), Parkinson's disease and other diseases with a motor disorder component, by intracranial toxin administration (U.S. Pat. No. 6,306,403), hair growth and hair retention (U.S. Pat. No. 6,299,893), psoriasis and dermatitis (U.S. Pat. No. 5,670, 484), injured muscles (U.S. Pat. No. 6,423,319, various cancers (U.S. Pat. No. 6,139,845), pancreatic disorders (U.S. Pat. No. 6,143,306), smooth muscle disorders (U.S. Pat. No. 5,437,291, including injection of a *botulinum* toxin into the upper and lower esophageal, pyloric and anal sphincters) ), prostate disorders (U.S. Pat. No. 6,365,164), inflammation, arthritis and gout (U.S. Pat. No. 6,063,768), juvenile cerebral palsy (U.S. Pat. No. 6,395,277), inner ear disorders (U.S. Pat. No. 6,265,379), thyroid disorders (U.S. Pat. No. 6,358,513), parathyroid disorders (U.S. Pat. No. 6,328,977). Additionally, controlled release toxin implants are known (see e.g. U.S. Pat. Nos. 6,306,423 and 6,312,708).

A *botulinum* toxin has been used to treat recalcitrant restless leg syndrome (Kudelko, K.M., et al., *Successful treatment of recalcitrant Restless Legs Syndrome with botulinum toxin A*, Mov Disord 2002;17 (Suppl 5):S242). Restless leg syndrome (RLS) involves an uncomfortable sensation in muscles, usually in the legs and thighs that occurs most commonly in middle aged woman. The abnormal sensation is relieved by moving the legs. RLS is not an obsessive compulsive disorder because it is not characterized by either recurrent intrusive thoughts or ritualistic behaviors. The amount of a *botulinum* toxin administered to treat restless leg syndrome (i.e. 25-50 units of a type A *botulinum* toxin per leg) exceeds the amount of toxin typically used to reduce the tone of a hypertonic or rigid thigh muscle, and can indeed can cause some paralysis of the injected thigh muscle.

Additionally, the finger biting, lip biting and tongue biting self mutilation behaviors of Lesch Nyhan syndrome have been treated by injecting a *botulinum* toxin into the chewing or clenching muscles of the mouth in one patient. Dabrowski E., et al, *Botulinum toxin as a novel treatment for self-mutilation in Lesch-Nyhan syndrome*, Ann Neurol 2002 September; 52 (3 Supp 1): S157. Injection of the fingers, lips or tongue is believed contraindicated because of the ulceration and sensitivity of these extremities due to the injurious behaviors of the syndrome.

Furthermore, a *botulinum* toxin has been used to treat focal dystonic tics or muscle spasms of Tourette's syndrome. Jankovic, J., *Botulinum toxin in the treatment of tics associated with Tourette's syndrome*, Neurology 1993 April; 43 (4 Supp 2): A310; Jankovic, J., *Botulinum toxin in the treatment of dystonic tics*, Mov Disord 1994 May; 9(3): 347-9, and; Krauss J., et al., *Severe motor tics causing cervical myelopathy in Tourette's syndrome*, Mov Disord 1996; 11 (5): 563-6. These publications indicate that a *botulinum* toxin can act to treat a Tourette's syndrome tic both by reducing the force of contraction necessary to generate the muscle movement (i.e. by a partial paralysis of the tic involved muscles) as well as by an inhibition or resolution of the premonitory symptoms (i.e. by removing the urge to carry out or to accomplish the tic) which precede the tic. Unfortunately, significant neck pain, neck weakness and neck pain was reported in some of the Tourette's syndrome patient's administered a *botulinum* toxin to treat a neck tic. Additionally, the literature is contradictory with regard to use of a *botulinum* toxin to treat a Tourette's syndrome tic, as others have reported no relief upon use of *botulinum* toxin to treat a Tourette syndrome tic, even at dose levels that caused muscle weakness or paralysis. Chappell, P. B., et al., *Future therapies of Tourette syndrome*, Neurol Clin 1997 May; 15(2): 429-50, at 444.

*Tetanus* toxin, as well as derivatives (i.e. with a non-native targeting moiety), fragments, hybrids and chimeras thereof can also have therapeutic utility. The *tetanus* toxin bears many similarities to the *botulinum* toxins. Thus, both the *tetanus* toxin and the *botulinum* toxins are polypeptides made by closely related species of *Clostridium* (*Clostridium tetani* and *Clostridium botulinum*, respectively). Additionally, both the *tetanus* toxin and the *botulinum* toxins are dichain proteins composed of a light chain (molecular weight about 50 kD) covalently bound by a single disulfide bond to a heavy chain (molecular weight about 100 kD). Hence, the molecular weight of *tetanus* toxin and of each of the seven *botulinum* toxins (non-complexed) is about 150 kD. Furthermore, for both the *tetanus* toxin and the *botulinum* toxins, the light chain bears the domain which exhibits intracellular biological (protease) activity, while the heavy chain comprises the receptor binding (immunogenic) and cell membrane translocational domains.

Further, both the *tetanus* toxin and the *botulinum* toxins exhibit a high, specific affinity for gangliocide receptors on the surface of presynaptic cholinergic neurons. Receptor mediated endocytosis of *tetanus* toxin by peripheral cholinergic neurons results in retrograde axonal transport, blocking of the release of inhibitory neurotransmitters from central synapses and a spastic paralysis. Contrarily, receptor mediated endocytosis of *botulinum* toxin by peripheral cholinergic neurons results in little if any retrograde transport, inhibition of acetylcholine exocytosis from the intoxicated peripheral motor neurons and a flaccid paralysis.

Finally, the *tetanus* toxin and the *botulinum* toxins resemble each other in both biosynthesis and molecular architecture. Thus, there is an overall 34% identity between the protein sequences of *tetanus* toxin and *botulinum* toxin type A, and a sequence identity as high as 62% for some functional domains. Binz T. et al., *The Complete Sequence of Botulinum Neurotoxin Type A and Comparison with Other Clostridial Neurotoxins*, J Biological Chemistry 265(16);9153-9158: 1990.

Acetylcholine

Typically only a single type of small molecule neurotransmitter is released by each type of neuron in the mammalian nervous system, although there is evidence which suggests that several neuromodulators can be released by the same neuron. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the bag 1 fibers of the muscle spindle fiber, by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. *Botulinum* toxin inhibits the release of both types of compounds from both types of cells in vitro, permeabilized (as by electroporation) or by direct injection of the toxin into the denervated cell. *Botulinum* toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

What is needed therefore is a non-surgical method for effectively treating effectively treating inappropriate, compulsive, ritualistic and/or obsessive behaviors characterized by repetitive, unproductive motor activity.

SUMMARY

The present invention meets this need and provides methods for effectively treating inappropriate, compulsive, ritualistic and/or obsessive behaviors characterized by repetitive, unproductive motor activity with a low dose of a *Clostridial* toxin.

A method according to my invention can be carried out by administration of a *Clostridial* toxin to a patient with an obsessive disorder and/or with a compulsive disorder. As used herein "obsessive compulsive disorder" means an obsessive disorder or a compulsive disorder, or a disorder which combines elements of both obsession and compulsion. "Treating" means to alleviate (or to eliminate) at least one symptom, either temporarily or permanently. The *Clostridial* toxin is preferably a *botulinum* toxin (as either a complex or as a pure [i.e. about 150 kDa molecule], such as a *botulinum* toxin A, B, C, D, E, F or G. Administration of the *Clostridial* toxin can be by a transdermal route (i.e. by application of a *Clostridial* toxin in a cream, patch or lotion vehicle), subdermal route (i.e. subcutaneous or intramuscular) or by an intradermal route of administration.

A hypothesized physiological reason for the efficacy of my invention, as explained in greater detail below, is to reduce, inhibit or eliminate particular sensory input (afferent) from the periphery into the central nervous system (including to the brain) which sensory input is believed to precede and to be pivotal to the initiation of a repetitive, unproductive motor activity. Such inappropriate sensory input can be attenuated or eliminated by targeting sensory neurons located within muscle tissues or that are located in or under the skin with a low dose of a *Clostridial* toxin.

The dose of a *Clostridial* toxin used according to the present invention is much less than the amount of toxin that would be used to paralyze a muscle (and is even less than the amount of the toxin used to reduce a rigid muscle tone), since the intent of a method according to the present invention is not to paralyze a muscle or to reduce the tone of a rigid muscle, but to reduce an undesirable sensory output from sensory neurons located in or a muscle or in or under the skin. Additionally, the low dose of the *Clostridial* toxin is selected with a volume to preferably achieve a toxin distribution to multiple sites of undesirable afferent sensory signals, such as from spindle fibers or secretory cells in the skin or subdermally.

Excluded from the scope of present invention is administration (as by intramuscular injection) of a *Clostridial* toxin (such as a *botulinum* toxin) into any neck muscles (such as into the splenii muscles) of a patient because such a local administration of toxin can result, particularly in adolescent patients, in poor head orientation ("floppy head"), prolonged neck pain, neck weakness and/or neck stiffness and/or exacerbation of a pre-existing neck or spinal injury (often due to the tic itself). Additionally, the complex neurological nature of Tourette's syndrome and the contradictory state of the art with regard to Tourette's syndrome tics contraindicate use of a *botulinum* toxin to treat a symptom of Tourette's syndrome. Thus, treatment of focal dystonic neck tics, such as the neck tics associated with Tourette's syndrome, is excluded from the scope of the present invention, as being better treated by head restraints, behavioral modification therapy and/or proven pharmacologic agents, such as TCAs or SSRIs.

Thus, my invention is a pharmacologic method for treating inappropriate, compulsive, ritualistic and/or obsessive behaviors characterized by repetitive, unproductive motor activity, which are not neck tics. My invention can be practised by administering a low dose of a *Clostridial* toxin to the muscle or muscle group which appears to initiates the repetitive, unproductive motor activity (i.e. to treat repetitive head banging). Alternately my invention can be practised by administering a low dose of a *Clostridial* toxin to intradermal or subdermal sensory neurons which apparently generate an urge, itch or sensation which precedes the repetitive motor activity (i.e. skin picking). As explained above, my invention is not suitable for the treatment for any neck tics (whether motor or vocal), and additionally does not encompass treatment of any muscle spasms. "Low dose" means an amount of the *Clostridial* toxin (such as a *botulinum* toxin) which is sufficient to inhibit a sensory output from a muscle to the CNS, but which is insufficient to cause either clinically significant muscle paralysis, weakness or hypotonicity.

The following definitions also apply herein:

"About" means approximately or nearly and in the context of a numerical value or range set forth herein means ±10% of the numerical value or range recited or claimed.

"Alleviating" means a reduction in the occurrence of the disorder. Thus, alleviating includes some reduction (so that the disorder is practised for fewer than, or appears in fewer than, than six hours out of a twenty-four hour period), significant reduction (so that the disorder is practised for fewer than, or appears in fewer than, three hours out of a twenty-four hour period), near total reduction (so that the disorder is practised for fewer than, or appears in fewer than, one hour out of a twenty-four hour period), and total reduction of the disorder. An alleviating effect may not appear clinically for between 1 to 7 days after administration of a *Clostridial* toxin to a patient "*Botulinum* toxin" means a *botulinum* neurotoxin as either pure toxin or complex, and excludes *botulinum* toxins which are not neurotoxins such as the cytotoxic *botulinum* toxins $C_2$ and $C_3$.

"Disorder" means an inappropriate, compulsive, ritualistic and/or obsessive behaviors characterized by repetitive, unproductive motor activity, which are not neck tics. Specific obsessive compulsive disorders are defined as set forth in the DSM-IVR.

"Local administration" means peripheral administration (i.e. by a subcutaneous, intramuscular, subdermal or transdermal route) of a pharmaceutical agent to or to the vicinity of a muscle or of a subdermal location of a patient by a non-systemic route. Thus, local administration excludes systemic (i.e. to the blood circulation system) routes of administration, such as intravenous or oral administration. Peripheral administration means administration to the periphery (i.e. to a location on or within a limb, trunk or head of a patient) as opposed to a visceral or gut (i.e. to the viscera) administration. An example of local administration is intramuscular injection of a pharmaceutical agent to a head or facial muscle or subdermal location of a patient.

Methods for treating a disorder characteristic by inappropriate, compulsive, ritualistic and/or obsessive behaviors characterized by repetitive, unproductive motor activity with a low dose of a *Clostridial* toxin comprise the step of local administration of *Clostridial* neurotoxin to a patient. The *Clostridial* neurotoxin is administered in a therapeutically effective amount to alleviate at least one symptom of the disorder.

A suitable *Clostridial* neurotoxin may be a neurotoxin made by a bacterium, for example, the neurotoxin may be made from a *Clostridium botulinum, Clostridium butyricum*, or *Clostridium beratti*. In certain embodiments of the invention, the disorders are treated by intramuscular administration a *botulinum* toxin to the patient. The *botulinum* toxin may be a *botulinum* toxin type A, type B, type $C_1$, type D, type E, type F, or type G. The effects of the *botulinum* toxin may persist for between about 1 month and 5 years. The *botulinum* neurotoxin can be a recombinantly made *botulinum* neurotoxins, such as *botulinum* toxins produced by *E. coli*. In addition or alternatively, the *botulinum* neurotoxin can be a modified neurotoxin, that is a *botulinum neurotoxin* which has at least one of its amino acids deleted, modified or replaced, as compared to a native or the modified *botulinum* neurotoxin can be a recombinant produced *botulinum* neurotoxin or a derivative or fragment thereof.

The *botulinum* neurotoxin is administered to a peripheral site that is believed to be involved in the disorder being treated. The *botulinum* neurotoxin can be administered to a muscle which appears to initiate the disorder and can alleviate the symptoms within a few hours or within a few days after administration.

A method for treating a head banging disorder according to the present invention can comprise the step of local administration of a *botulinum* toxin to a patient with a head banging disorder to thereby alleviate the head banging disorder. The *botulinum* toxin can be selected from the group consisting of *botulinum* toxin types A, B, C, D, E, F and G. *Botulinum* toxin type A is a preferred *botulinum* toxin. The *botulinum* toxin can be administered (for example between about 1-50 units of a *botulinum* toxin type A or between about 50 to 2,500 units of a *botulinum* toxin type B) in an amount of between about 1 unit and about 2,500 units and the alleviation of the disorder can persist for between about 1 month and about 5 years. The local administration of the *botulinum* toxin can be to a head or facial muscle. The local administration can be by intramuscular injection. Alternately, the local administration of the *botulinum* toxin can be to a dermal or subdermal location or to a muscle location from which the patient perceives the existence of a premonitory sensation, which leads to the generation of the disorder, to arise.

A detailed embodiment of my invention can comprise a method for treating a head banging disorder, the method comprising a step of local administration to a head of a patient with a head banging disorder of between about 1 unit and about 1,500 units of a *botulinum* toxin type A, thereby alleviating the head banging disorder for between about 1 month and about 5 years.

DESCRIPTION

The present invention is based on the discovery that peripheral administration of a low dose of a *Clostridial* toxin (such as a *botulinum* toxin) can provide effective treatment or relief of inappropriate, compulsive, ritualistic and/or obsessive behaviors characterized by repetitive, unproductive motor activity. Thus, a *botulinum* toxin (such as a *botulinum* toxin serotype A, B, $C_1$, D, E, F or G) can be injected into a muscle which initiates (or acts to recruit other muscles to) the undesirable repetitive behavior to thereby suppress and treat such an undesirable and/or self injurious motoric behavioral characteristic. Alternately, the *botulinum* toxin can be administered to an intradermal or subdermal sensory neuron thereby suppress and treat such an undesirable and/or self injurious motoric behavioral characteristic.

Without wishing to be bound by theory a physiological mechanism can be proposed for the efficacy of the present invention. It is known that muscles have a complex system of innervation and sensory output. Thus, anterior motor neurons located in each segment of the anterior horns of the spinal cord gray matter give rise to efferent alpha motor neurons and efferent gamma motor neurons that leave the spinal cord by way of the anterior roots to innervate skeletal (extrafusal) muscle fibers. The alpha motor neurons cause contraction of extrafusal skeletal muscle fibers while the gamma motor neurons innervate the intrafusal fibers of skeletal muscle. As well as excitation by these two type of efferent anterior motor neuron projections, there are additional, afferent sensory neurons which project from muscle spindle and golgi tendon organs and act to transmit information regarding various muscle parameter status to the spinal cord, cerebellum and cerebral cortex. These afferent motor neurons which relay sensory information from the muscle spindle include type Ia and type II sensory afferent neurons. See e.g. pages 686-688 of Guyton A. C. et al., *Textbook of Medical Physiology*, W. B. Saunders Company 1996, ninth edition.

Significantly, it has been determined that a *botulinum* toxin can act to reduce transmission of sensory information from muscle type Ia afferent neurons. Aoki, K., *Physiology and pharmacology of therapeutic botulinum neurotoxins*, in Kreyden, 0., editor, Hyperhydrosis and *botulinum* toxin in dermatology, Basel, Karger; 2002; 30: pages 107-116, at 109-110. And it has been hypothesized that *botulinum* toxin can have a direct effect upon muscle cell sensory afferents and modify signals from these afferents to the central nervous system. See e.g. Brin, M., et al., *Botulinum toxin type A: pharmacology*, in Mayer N., editor, Spasticity: etiology, evaluation, management and the role of *botulinum* toxin, 2002; pages 110-124, at 112-113; Gui, M., et al., *Mechanisms of the antinociceptive effect of subcutaneous BOTOX®* (a *botulinuin* toxin type A complex): *inhibition of peripheral and central nociceptive processing*, Naunyn Schmiedebergs Arch Pharmacol 2002; 365 (supp 2): R17. Aoki, K., et al., *Botulinum toxin type A and other botulinum toxin serorypes: a comparative review of biochemical and pharmacological actions*, Eur J. Neurol 2001: (suppl 5); 21-29. Thus, it has been demonstrated that *botulinum* toxin can cause an altered sensory output from muscle to CNS and brain.

Importantly, the sensory neurons from which afferent output is to be inhibited by a method according to the present invention need not be located on or within a muscle, but can be in an intradermal or subdermal location.

It can be postulated that obsessive-compulsive disorders are due to disinhibition of a central nervous system control process. Thus, a disinhibition reverberatory circuit may exist between the head of the caudate nucleus and the thalamus and between the thalamus and the frontorbito neurons which is sensitive to signals arising from peripheral sensory information afferent from muscle neurons. Administration of a *botulinum* toxin to a muscles or skin to reduce sensory output from the muscle can permit the brain to regain adequate inhibition control of the obsessive-compulsive disorder motor behaviors, by preventing central generation of a premonitory urge to carry out the obsessive-compulsive disorder behavior. Notably, It has been reported that local administration of a *botulinum* toxin to neck muscles can apparently act to reduce generation of the premonitory urge associated with some Tourette's syndrome tics. Jankovic, J., *Botulinum toxin in the treatment of tics associated with Tourette's syndrome*, Neurology 1993 April; 43 (4 Supp 2): A310; Jankovic, J., *Botulinum toxin in the treatment of dystonic tics*, Mov Disord 1994 May; 9(3): 347-9, and; Krauss J., et al., *Severe motor tics causing cervical myelopathy in Tourette's syndrome*, Mov Disord 1996; 11(5): 563-6. Additionally, as previously discussed relatively high (paralytic effect) thigh muscle doses of a *botulinum* toxin have been used to treat restless leg syndrome, and injection of *botulinum* toxin into the chewing muscle has been used to treat the lip, tongue and finger biting behaviors of Lesch Nyhan syndrome.

It is my hypothesis that signals transmitted by afferent nerves which innervate muscles (i.e. muscle spindle fibers and muscle pain fibers) or from sensory structures in the skin or subdermally induce a sensory state which contributes in susceptible individuals to the generation of obsessive-compulsive disorder behaviors. That is, afferent signal from muscles or skin structures provide sensory information to the brain which then leads to the generation of a complex motor output in susceptible individuals, such as the self mutilation, obsessive hand washing, hair pulling, or other repetitive behaviors of obsessive-compulsive disorder. Thus, a local administration of a low dose of a *botulinum* toxin to muscle spindle fibers, pain fibers or other sensors in or in the vicinity of a muscle can act to alter the neural signal afferent output from these muscles to the brain and thereby decreasing neural (to brain) input and inhibit the undesirable obsessive-compulsive disorder behavior by preventing generation of a premonitory urge.

Important elements of my invention are firstly that is practised by use of a local administration of low dose of a *botulinum* toxin. The selected low dose causes neither muscle paralysis, weakness nor muscle hypotonicity. Secondly, the invention is practised by local administration of the low dose of the *botulinum* toxin to the muscle or to the muscle group which initiates the undesirable motor behavior. For example, with regard to obsessive finger biting the *botulinum* toxin is administered to the hand or forearm muscles. With regard to ritualistic checking and counting behaviors, the *botulinum* toxin is administered to the head muscles, such as scalp, forehead or facial muscles on the basis that such behaviors are initiated by sensory input from such muscle.

Conditions treatable by the present invention include skin picking, hair pulling, head banging, body rocking, counting, checking, and hoarding behaviors which are inappropriate, compulsive, ritualistic and/or obsessive behaviors characterized by repetitive, unproductive motor activity, which are not neck tics.

In compulsive skin picking there is often a psychotic sensation of skin crawling with the common description of perception of movement hypodermally. This sensation may very well be due to premonitory urges triggered by skin associated tiny muscle structures such as the arrector pili muscles of hair follicles, smooth muscle vasculature of the dermis or neural sensory structures within the skin. Thus, hypodermal (subcutaneous) injection into the dermis of a *Clostridial* toxin can be expected to focally relieve or block this sensation for several months.

Other disorders treatable by a method within the scope of the present invention include conditions with stereotypic movements such as Downs Syndrome, pervasive developmental disorder, developmental movement disorder, autism (hand/finger movement subtype), Asperger's Syndrome (hand/finger movement type) and Rhett's Syndrome (hand-washing movements).

The administration of the *Clostridial* toxin is carried out so as to target, for example, focal motoric movements of obsessive compulsive disorders. Thus, for repetitive hand washing behavior the toxin can be injected into the forearm muscles associated with washing movements, or into the hands based upon a pattern for the treatment of hyperhydrosis or a combination thereof. Treatment sites and doses can be selected based upon the muscles which initiate the observed movement at doses which do not produce significant muscle weakness. Thus, an injection pattern is selected to focus on the muscles which initiate the observed inappropriate movements.

The amount of the *Clostridial* toxin administered according to a method within the scope of the disclosed invention can vary according to the particular disorder being treated, its severity and other various patient variables including size, weight, age, and responsiveness to therapy. To guide the practitioner, typically, no less than about 1 unit and no more than about 25 units of a *botulinum* toxin type A (such as BOTOX®, a *botulinum* toxin type A complex) is administered per injection site, per patent treatment session. For a *botulinum* toxin type A such as DYSPORT® (a *botulinum* toxin type A complex), no less than about 2 units and no more about 125 units of the *botulinum* toxin type A are administered per injection site, per patent treatment session. For a *botulinum* toxin type B such as MYOBLOC® (a *botulinum* toxin type B preparation), no less than about 40 units and no more about 1500 units of the *botulinum* toxin type B are administered per injection site, per patent treatment session. Less than about 1, 2 or 40 units (of BOTOX® (a *botulinum* toxin tyre A complex), DYSPORT® (a *botulinum* toxin type A complex) and MYOBLOC® (a *botulinum* toxin type B prenaration), respectively) can fail to achieve a desired therapeutic effect, while more than about 25, 125 or 1500 units (of BOTOX® (a *botulinum* toxin type A complex), DYSPORT® (a *botulinum* toxin type A complex) and MYOBLOC® (a *botulinum* toxin type B prenaration), respectively) can result in significant muscle hypotonicity, weakness and/or paralysis, all of which are undesirable outcomes in a practise of the disclosed invention because the purpose of my invention is to treat inappropriate , compulsive, ritualistic and/or obsessive behaviors characterized by repetitive, unproductive motor activity, which are not neck tics, with a low dose of a *Clostridial* toxin to the muscle or muscle group which appears to initiates the repetitive, unproductive motor activity, the dose being sufficient to inhibit a sensory output from a muscle to the CNS, but insufficient to cause either significant muscle paralysis, weakness or hypotonicity.

More preferably: for BOTOX® (a *botulinum* toxin type A complex) no less than about 2 units and no more about 20 units of a *botulinum* toxin type A; for DYSPORT® (a *botulinum* toxin type A complex) no less than about 4 units and no more than about 100 units, and; for MYOBLOC® (a *botulinum* toxin type B preparation) no less than about 80 units and no more than about 1000 units are, respectively, administered per injection site, per patent treatment session.

Most preferably: for BOTOX® (a *botulinum* toxin type A complex) no less than about 5 units and no more about 15 units of a *botulinum* toxin type A; for DYSPORT® (a *botulinum* toxin type A complex) no less than about 20 units and no more than about 75 units, and; for MYOBLOC® (a *botulinum* toxin type B preparation), no less than about 200 units and no more than about 750 units are, respectively, administered per injection site, per patent treatment session. It is important to note that there can be multiple injection sites (i.e. a pattern of injections) for each patient treatment session.

Although examples of routes of administration and dosages are provided, the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14$^{th}$ edition, published by McGraw Hill). For example, the route and dosage for administration of a neurotoxin according to the present disclosed invention can be selected based upon criteria such as the solubility characteristics of the neurotoxin chosen as well as the intensity of the disorder as perceived by the patient.

The present invention is based on the discovery that peripheral administration of a *Clostridial* toxin can provide significant and long lasting relief from a variety of different obsessive-compulsive disorders. Peripheral administration permits a *Clostridial* toxin to be locally administered at a site, at or near a patient's muscle that has a direct effect on the neurons involved in the disorders, The *Clostridial* toxins used in accordance with the invention disclosed herein can inhibit transmission of chemical or electrical signals between select neuronal groups that are involved in generation of an obsessive-compulsive disorder. The *Clostridial* toxins preferably are not cytotoxic to the cells that are exposed to the *Clostridial* toxin. The *Clostridial* toxin can inhibit neurotransmission by reducing or preventing exocytosis of neurotransmitter from the neurons exposed to the *Clostridial* toxin. Or, the applied *Clostridial* toxins may reduce neurotransmission by inhibiting the generation of action potentials of the neurons exposed to the toxin. The suppressive effects provided by the *Clostridial* toxin should persist for a relatively long period of time, for example, for more than two months, and potentially for several years.

Examples of *Clostridial* toxins within the scope of the present invention include neurotoxins made by *Clostridium botulinum, Clostridium butyricum* and *Clostridium beratti* species. In addition, the *botulinum* toxins used in the methods of the invention may be a *botulinum* toxin selected from a group of *botulinum* toxin types A, B, C, D, E, F, and G. In one embodiment of the invention, the *botulinum* neurotoxin administered to the patient is *botulinum* toxin type A. *Botulinum* toxin type A is desirable due to its high potency in humans, ready availability, and known use for the treatment of skeletal and smooth muscle disorders when locally administered by intramuscular injection. The present invention also includes the use of (a) *Clostridial* neurotoxins obtained or processed by bacterial culturing, toxin extraction, concentration, preservation, freeze drying, and/or reconstitution; and/ or (b) modified or recombinant neurotoxins, that is neurotoxins that have had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made. These neurotoxin variants retain the ability to inhibit neurotransmission between or among neurons, and some of these variants may provide increased durations of inhibitory effects as compared to native neurotoxins, or may provide enhanced binding specificity to the neurons exposed to the neurotoxins. These neurotoxin variants may be selected by screening the variants using conventional assays to identify neurotoxins that have the desired physiological effects of inhibiting neurotransmission.

*Botulinum* toxins for use according to the present invention can be stored in lyophilized, vacuum dried form in containers under vacuum pressure or as stable liquids. Prior to lyophilization the *botulinum* toxin can be combined with pharmaceutically acceptable excipients, stabilizers and/or carriers, such as albumin. The lyophilized material can be reconstituted with saline or water to create a solution or composition containing the *botulinum* toxin to be administered to the patient.

Although the composition may only contain a single type of neurotoxin, such as *botulinum* toxin type A, as the active ingredient to suppress neurotransmission, other therapeutic compositions may include two or more types of neurotoxins, which may provide enhanced therapeutic effects of the disorders. For example, a composition administered to a patient may include *botulinum* toxin type A and *botulinum* toxin type B. Administering a single composition containing two different neurotoxins may permit the effective concentration of each of the neurotoxins to be lower than if a single neurotoxin is administered to the patient while still achieving the desired therapeutic effects. The composition administered to the patient may also contain other pharmaceutically active ingredients, such as, protein receptor or ion channel modulators, in combination with the neurotoxin or neurotoxins. These modulators may contribute to the reduction in neurotransmission between the various neurons. For example, a composition may contain gamma aminobutyric acid (GABA) type A receptor modulators that enhance the inhibitory effects mediated by the $GABA_A$ receptor. The $GABA_A$ receptor inhibits neuronal activity by effectively shunting current flow across the cell membrane. $GABA_A$ receptor modulators may enhance the inhibitory effects of the $GABA_A$ receptor and reduce electrical or chemical signal transmission from the neurons. Examples of $GABA_A$ receptor modulators include benzodiazepines, such as diazepam, oxaxepam, lorazepam, prazepam, alprazolam, halazeapam, chordiazepoxide, and chlorazepate. Compositions may also contain glutamate receptor modulators that decrease the excitatory effects mediated by glutamate receptors. Examples of glutamate receptor modulators include agents that inhibit current flux through AMPA, NMDA, and/or kainate types of glutamate receptors. The compositions may also include agents that modulate dopamine receptors, such as antipsychotics, norepinephrine receptors, and/or serotonin receptors. The compositions may also include agents that affect ion flux through voltage gated calcium channels, potassium channels, and/or sodium channels. Thus, the compositions used to treat obsessive compulsive disorders may include one or more neurotoxins, such as *botulinum* toxins, in addition to ion channel receptor modulators that may reduce neurotransmission.

The neurotoxin may be administered by any suitable method as determined by the attending physician. The methods of administration permit the neurotoxin to be administered locally to a selected target tissue. Methods of administration include injection of a solution or composition containing the neurotoxin, as described above, and include implantation of a controlled release system that controllably releases the neurotoxin to the target tissue. Such controlled release systems reduce the need for repeat injections. Diffusion of biological activity of a *botulinum* toxin within a tissue appears to be a function of dose and can be graduated. Jankovic J., et al *Therapy With Botulinum Toxin*, Marcel Dekker, Inc., (1994), page 150. Thus, diffusion of *botulinum* toxin can be controlled to reduce potentially undesirable side effects that may affect the patient's cognitive abilities. For example, the neurotoxin may be administered so that the neurotoxin primarily effects neural systems believed to be involved in the obsessive compulsive disorder, and does not have negatively adverse effects on other neural systems.

A polyanhydride polymer, Gliadel® (Stolle R & D, Inc., Cincinnati, Ohio) a copolymer of poly-carboxyphenoxypropane and sebacic acid in a ratio of 20:80 has been used to make implants, and has been intracranially implanted to treat malignant gliomas. Polymer and BCNU can be co-dissolved in methylene chloride and spray-dried into microspheres. The microspheres can then be pressed into discs 1.4 cm in diameter and 1.0 mm thick by compression molding, packaged in aluminum foil pouches under nitrogen atmosphere and sterilized by 2.2 megaRads of gamma irradiation. The polymer permits release of carmustine over a 2-3 week period, although it can take more than a year for the polymer to be largely degraded. Brem, H., et al, *Placebo-Controlled Trial of Safety and Efficacy of Intraoperative Controlled Delivery by Biodegradable Polymers of Chemotherapy for Recurrent Gliomas*, Lancet 345; 1008-1012:1995.

Implants useful in practicing the methods disclosed herein may be prepared by mixing a desired amount of a stabilized neurotoxin (such as non-reconstituted BOTOX®, a *botulinum* toxin type A complex) into a solution of a suitable polymer dissolved in methylene chloride. The solution may be prepared at room temperature. The solution can then be transferred to a Petri dish and the methylene chloride evaporated in a vacuum desiccator. Depending upon the implant size desired and hence the amount of incorporated neurotoxin, a suitable amount of the dried neurotoxin incorporating implant is compressed at about 8000 p.s.i. for 5 seconds or at 3000 p.s.i. for 17 seconds in a mold to form implant discs encapsulating the neurotoxin. See e.g. Fung L. K. et al., *Pharmacokinetics of Interstitial Delivery of Carmustine 4-HydroperoAycyclophospharnide and Paclitaxel From a Biodegradable Polymer Implant in the Monkey Brain*, Cancer Research 58;672-684:1998.

Local administration of a *Clostridial* toxin, such as a *botulinum* toxin, can provide a high, local therapeutic level of the toxin. A controlled release polymer capable of long term, local delivery of a *Clostridial* toxin to a target muscle permits effective dosing of a target tissue. A suitable implant, as set forth in U.S. Pat. No. 6,306,423 entitled "Neurotoxin Implant", allows the direct introduction of a chemotherapeutic agent to a target tissue via a controlled release polymer. The implant polymers used are preferably hydrophobic so as to protect the polymer incorporated neurotoxin from water induced decomposition until the toxin is released into the target tissue environment.

Local administration of a *botulinum* toxin, according to the present invention, by injection or implant to a target tissue provides a superior alternative to systemic administration of pharmaceuticals to patients to alleviate the symptoms associated with the disorders treated.

The amount of a *Clostridial* toxin selected for local administration to a target tissue according to the present disclosed invention can be varied based upon criteria such as the disorder being treated, its severity, the extent of muscle tissue to be treated, solubility characteristics of the neurotoxin toxin chosen as well as the age, sex, weight and health of the patient. For example, the extent of the area of muscle tissue influenced is believed to be proportional to the volume of neurotoxin injected, while the quantity of the suppressant effect is, for most dose ranges, believed to be proportional to the concentration of a *Clostridial* toxin administered. Methods for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., $14^{th}$ edition, published by McGraw Hill).

Significantly, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assessed using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality, and general health perceptions. Scores obtained can be compared to published values available for various general and patient populations.

EXAMPLES

The following non-limiting examples provide those of ordinary skill in the art with specific preferred methods to treat conditions within the scope of the present invention and are not intended to limit the scope of the invention. In the following examples various modes of non-systemic administration of a *Clostridial* neurotoxin can be carried out. For example, by intramuscular injection, subcutaneous injection or by implantation of a controlled release implant.

Example 1

*Botulinum* Toxin Type A Therapy for Head Banging

A 15 year old male bangs his head on walls and on his school desk without obvious triggers. He reports 20-25 head banging episodes a day. Upon examination he relates that he is lonely and feels an urge to, and gratification upon, carrying out the chronic head banging. His forehead is bruised and tender to the touch. The patient is treated by intramuscular injection of 5 units of a *botulinum* toxin type A (i.e. BOTOX®, a *botulinum* toxin type A complex) into the forehead muscles bilaterally at two different locations (10 units toxin total). Within 1-7 days after toxin administration the patient report that he now banging his head only once or twice a day and such an alleviation of his condition persists for 4-6 months. For extended therapeutic relief (1 to 5 years), one or more polymeric implants incorporating a suitable quantity of a *botulinum* toxin type A can be placed at the target tissue site.

A *botulinum* toxin type B, C, D, E, F or G can be substituted for the *botulinum* toxin type A used above, for example by use of 250 units of a *botulinum* toxin type B.

Example 2

*Botulinum* Toxin Type A Therapy for Repetitive Hand Washing

A 46 year old male presents with red, chapped hands. He relates compulsive washing of his hands for 6 to 8 hours a day, often after normal hygiene activities. The patient is treated by intramuscular injection of 5 units of a *botulinum* toxin type A (i.e. BOTOX® a *botulinum* toxin type A complex) into the forearm muscles bilaterally at two different locations (10 units toxin, per arm). Within 1-7 days after toxin administration the patient report that he is washing his hands now for less than one hour a day and alleviation of his condition persists for 4-6 months. For extended therapeutic relief (1 to 5 years), one or more polymeric implants incorporating a suitable quantity of a *botulinum* toxin type A can be placed at the target tissue site.

Example 3

*Botulinum* Toxin Type B Therapy for Repetitive Hand Washing

A 22 year old female presents with red, chapped hands. She relates compulsive washing of hers hands for 7 to 9 hours a day, often after normal hygiene activities. She relates perception in her hands of an urge to wash them. The patient is treated by intramuscular injection of 225 units of a *botulinum* toxin type B (i.e. MYOBLOC®) into the palm of each of her hands. Within 1-7 days after toxin administration the patient report that she is washing her hands now for less than one half hour a day and alleviation of the condition persists for 4-6 months. For extended therapeutic relief (1 to 5 years), one or more polymeric implants incorporating a suitable quantity of a *botulinum* toxin type B can be placed at the target tissue site.

A *botulinum* toxin type C, D, E, F or G can be substituted for the *botulinum* toxin type A or B used in the examples above.

Example 4

*Botulinum* Toxin Therapy for Trichotillomania

A sixteen year old girl with normal intelligence is referred by her dermatologist and examined for several, irregular bald patches on her head. The hair loss is on the contralateral side of the dominant hand and the affected areas include broken hairs of varying lengths with skin discoloration secondary to rubbing the scalp. The child admits to pulling her hair because "I'm depressed." Adrenal function is normal and trichotillomania is diagnosed. The patient's trichotillomania showed nominal response to antidepressant medication, including tricyclic antidepressants (desipramine and imipramine), as these medications resulted in a brief 2-3 day remission of the hair pulling. Other therapeutic interventions included cognitive behavioral therapy and counseling, both of which were unsuccessful, despite attendance. The child is treated by intramuscular injection of 5 units of a *botulinum* toxin type A (i.e. BOTOX®, a *botulinum* toxin type A complex) into the frontalis and occipitalis muscles (10 units toxin, per treatment session). Alternately, so as to achieve a wider distribution of the *botulinum* toxin, 100 units of a *botulinum* toxin type A in 5 ml of saline can be injected into multiple (about 20 sites) scalp locations. Within 1-7 days after toxin administration the patient report that she has stopped pulling her hair and alleviation of her condition persists for 4-6 months. For extended therapeutic relief (1 to 5 years), one or more polymeric implants incorporating a suitable quantity of a *botulinum* toxin type A can be placed at the target tissue site.

A *botulinum* toxin type B, C, D, E, F or G can be substituted for the *botulinum* toxin type A used above, for example by use of 250 units of a *botulinum* toxin type B.

Example 5

*Botulinum* Toxin Type A Therapy for Dermatillomania

A 57 year old married woman is examined for chronic skin picking over the last 3 years to her arms and legs, never leaving the lesions alone long enough to heal. Prior to clinical presentation she has tried alternative treatment approaches for the picking, including acupuncture, dermatology consultation, and group therapy. She picked with her fingernails and often ingests the scabs after removal. She relates and urge which builds up and which is relieved by the picking. Her condition is recalcitrant to behavior modification therapy, fluoxetine and venlafaxine. After informed consent, 4 units of a *botulinum* toxin type A (i.e. BOTOX®, a *botulinum* toxin type A complex) are injected subdermally at the locations of the chronic skin picking. Alternately, so as to achieve a wider distribution of the *botulinum* toxin, 100 units of a *botulinum* toxin type A in 5 ml of saline can be injected into multiple (about 20) sites of the skin picking. Within 1-7 days after toxin administration the patient has stopped picking her skin and alleviation of her condition persists for 4-6 months. For extended therapeutic relief (1 to 5 years), one or more polymeric implants incorporating a suitable quantity of a *botulinum* toxin type A can be placed at the target tissue site.

Example 6

*Botulinum* Toxin Type B Therapy for Dermatillomania

A 26 year old, divorced, college educated man seeks treatment for his chronic, self injurious skin picking. He describes an awareness of clogged pores on his face, especially around his nose and chin which he ties to unclog with his fingernails. The target of his skin picking includes "raised skin" as well as healthy skin. Skin picking episodes end when his skin becomes inflamed or bleeding. He reports about 20 skin picking episodes every day, with each episode lasting 1 to five minutes. He relates feeling tension or nervousness build up before the skin picking and relief after he has picked. 200 units of a *botulinum* toxin type B is are injected subdermally at three separate the locations of the chronic facial skin picking. Alternately, so as to achieve a wider distribution of the *botulinum* toxin, 5000 units of a *botulinum* toxin type B in 5 ml of saline can be injected into multiple (about 20) sites of the skin picking. Within 1-7 days after toxin administration the patient has stopped picking his skin and alleviation of the condition persists for 4-6 months. For extended therapeutic relief (1 to 5 years), one or more polymeric implants incorporating a suitable quantity of a *botulinum* toxin type B can be placed at the target tissue site.

A *botulinum* toxin type C, D, E, F or G can be substituted for the *botulinum* toxin type A or B used in the examples above.

Example 7

*Botulinum* Toxin Type A Therapy for Finger Biting

An eight year old boy with mild mental retardation bites his fingers hands regularly and his fingers have become ulcerated. He mother reports that he will bite his fingers continuously unless restrained. The patient is treated by intramuscular injection of 3 units of a *botulinum* toxin type A (i.e. BOTOX®, a *botulinum* toxin type A complex) into the base of each finger on each hand. Alternately, the forearm muscles can be injected bilaterally with 10 units of the *botulinum* toxin. Within 1-7 days after toxin administration the finger biting has completely subsided and resolved. His fingers heal and this alleviation of his condition persists for 4-6 months. For extended therapeutic relief (1 to 5 years), one or more polymeric implants incorporating a suitable quantity of a *botulinum* toxin type A can be placed at the target tissue site.

A *botulinum* toxin type B, C, D, E, F or G can be substituted for the *botulinum* toxin type A used above, for example by use of 250 units of a *botulinum* toxin type B.

Example 8

*Botulinum* Toxin Type A Therapy for Pruritis Associated with Psychosis

A 26 year old married female is referred for pharmacologically recalcitrant skin itching which is described to feel as if an insect is crawling under her skin. On repeated instances when not restrained she has cut herself to "let out the bugs". Auditory and visual hallucinations are also present. The patient is treated 4 units of a *botulinum* toxin type A (i.e. BOTOX®, a *botulinum* toxin type A complex) are injected subdermally at the locations of the chronic skin itching. Alternately, so as to achieve a wider distribution of the *botulinum* toxin, 100 units of a *botulinum* toxin type A in 5 ml of saline can be injected into multiple (about 20) sites of the perceived skin itching. Within 1-7 days after toxin administration the patient reports relief from the skin itching and alleviation of her condition persists for 4-6 months. For extended therapeutic relief (1 to 5 years), one or more polymeric implants incorporatinga suitable quantity of a *botulinum* toxin type A can be placed at the target tissue site.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes peripheral administration methods to alleviate a disorder wherein two or more neurotoxins, such as two or more *botulinum* toxins, are administered concurrently or consecutively. For example, *botulinum* toxin type A can be administered until a loss of clinical response or neutralizing antibodies develop, followed by administration of *botulinum* toxin type B. Alternately, a combination of any two or more of the botulinum serotypes A-G can be locally administered to control the onset and duration of the desired therapeutic result. Furthermore, non-neurotoxin compounds can be administered prior to, concurrently with or subsequent to administration of the neurotoxin to proved adjunct effect such as enhanced or a more rapid onset of denervation before the neurotoxin, such as a *botulinum* toxin, begins to exert its therapeutic effect.

A method for treating a disorder according to the invention disclosed herein has many benefits and advantages, including the following:

1. the symptoms can be dramatically reduced.

2. the symptoms of an obsessive-compulsive disorder can be reduced for from about two to about six months per injection of neurotoxin and for from about one year to about five years upon use of a controlled release neurotoxin implant.

3. the injected or implanted neurotoxin exerts an intramuscular target tissue site specific suppression of neuronal activity.

4. the injected or implanted *Clostridial* neurotoxin shows little or no tendency to diffuse or to be transported away from the intramuscular (or intradermal or subdermal) injection or implantation site.

5. few or no significant undesirable side effects occur from intramuscular (or intradermal or subdermal) injection or implantation of the *Clostridial* neurotoxin.

6. the suppressant effects of the present methods can result in the desirable side effects of greater patient mobility, a more positive attitude, and an improved quality of life.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes local administration methods wherein two or more *Clostridial* neurotoxins, such as two or more *botulinum* toxins, are administered concurrently or consecutively. For example, *botulinum* toxin type A can be locally administered until a loss of clinical response or neutralizing antibodies develop, followed by administration of *botulinum* toxin type B. Furthermore, non-neurotoxin compounds can be locally administered prior to, concurrently with or subsequent to administration of the neurotoxin to provide adjunct effect such as enhanced or a more rapid onset of suppression before the neurotoxin, such as a *botulinum* toxin, begins to exert its more long lasting suppressant effect.

My invention also includes within its scope the use of a neurotoxin, such as a *botulinum* toxin, in the preparation of a medicament for the treatment of an obsessive-compulsive disorder, by local administration of the *Clostridial* neurotoxin.

All references, articles, patents, applications and publications set forth above are incorporated herein by reference in their entireties.

Accordingly, the spirit and scope of the following claims should not be limited to the descriptions of the preferred embodiments set forth above.

I claim:

1. A method for treating an obsessive compulsive head banging disorder, the method comprising the step of administration to a head muscle of a patient with an obsessive compulsive head banging disorder of between about 1 unit and about 1,500 units of a *botulinum* toxin type A, thereby treating the obsessive compulsive head banging disorder for between about 1 month and about 5 years.

2. The method of claim 1, wherein administration to head muscle of a patient is by local administration.

3. The method of claim 1, wherein local administration is by intramuscular injection.

4. The method of claim 1, wherein treating the obsessive compulsive head banging disorder is for between 4 to 6 months.

* * * * *